US012763596B2

(12) United States Patent
Shelton, IV et al.

(10) Patent No.: US 12,763,596 B2

(45) Date of Patent: Oct. 13, 2026

(54) ELECTRONIC POWER SYSTEM WITH MODULAR SEALED ENCLOSURE

(71) Applicant: CILAG GMBH INTERNATIONAL, Zug (CH)

(72) Inventors: Frederick E. Shelton, IV, Hillsboro, OH (US); Shane R. Adams, Lebanon, OH (US)

(73) Assignee: CILAG GMBH INTERNATIONAL, Zug (CH)

(*) Notice: Subject to any disclaimer, the term of this patent is extended or adjusted under 35 U.S.C. 154(b) by 223 days.

(21) Appl. No.: 18/659,244

(22) Filed: May 9, 2024

(65) Prior Publication Data

US 2025/0350134 A1 Nov. 13, 2025

(51) Int. Cl.

| | |
|---|---|
| ***H02P 1/00*** | (2006.01) |
| ***H02J 7/00*** | (2006.01) |
| ***H02P 23/00*** | (2016.01) |
| *A61B 17/068* | (2006.01) |

(52) U.S. Cl.

CPC .............. *H02J 7/855* (2026.01); *H02P 23/00* (2013.01); *A61B 17/068* (2013.01)

(58) Field of Classification Search

CPC ....... H02P 29/00; H02P 23/00; H02P 2201/09

See application file for complete search history.

(56) References Cited

U.S. PATENT DOCUMENTS

| | | | |
|---|---|---|---|
| 5,260,637 A | 11/1993 | Pizzi | |
| 9,005,230 B2 | 4/2015 | Yates | |
| 9,050,083 B2 | 6/2015 | Yates et al. | |
| 10,182,816 B2 | 1/2019 | Shelton, IV et al. | |
| 10,327,767 B2 | 6/2019 | Shelton, IV | |
| 10,327,769 B2 | 6/2019 | Overmyer | |
| 10,347,247 B2 | 7/2019 | Bhaya et al. | |
| 10,357,247 B2 | 7/2019 | Shelton, IV | |
| 10,973,563 B2 | 4/2021 | Houser et al. | |
| 2013/0214025 A1 | 8/2013 | Zemlok et al. | |
| 2015/0088127 A1* | 3/2015 | Craig | A61B 46/10 606/41 |
| 2017/0189096 A1* | 7/2017 | Danziger | A61B 18/1206 |
| 2017/0231609 A1 | 8/2017 | Gregg | |

FOREIGN PATENT DOCUMENTS

WO WO-2016187080 A1 * 11/2016 ............... A61L 2/28

* cited by examiner

Primary Examiner — Karen Masih

(74) *Attorney, Agent, or Firm* — Troutman Pepper Locke LLP

(57) ABSTRACT

The disclosed technology includes a sterilizable powered electronics system for a surgical instrument that includes a boost regulator circuit, an ultracapacitor, and a sealed enclosure. The boost regulator circuit is configured to electrically connect to one or more batteries and output at least one of a predetermined voltage or a predetermined current. The ultracapacitor is electrically connected to the boost regulator circuit. The sealed enclosure encloses the boost regulator circuit and is configured to withstand temperatures greater than 50° C. and pressures greater than 15 psi. At least one of the boost regulator circuit or the ultracapacitor can be configured to be electrically connected to an instrument motor.

18 Claims, 8 Drawing Sheets

| STERILIZER | TEMPERATURE | PRESSURE | TIME |
|---|---|---|---|
| STEAM AUTOCLAVE | 121°C (250°F) | 15 PSI | 15MIN |
| ▪ UNWRAPPED ITEMS | 121°C (250°F) | 30 PSI | 3MIN |
| ▪ LIGHTLY WRAPPED ITEMS | 132°C (270°F) | 30 PSI | 8MIN |
| ▪ TOTALLY WRAPPED ITEMS | 132°C (270°F) | 30 PSI | 10MIN |
| DRY HEAT WRAPPED | 170°C (340°F) | | 60 MIN |
| CHEMICAL VAPOR | 132°C (270°F) | 20-40 PSI | 20 MIN |
| ETHYLENE OXIDE | AMBIENT | | 8-10 HR |

*FIG. 6B*

AUTOCLAVE STANDARD STEAM STERILIZATION CYCLES

ELECTRONIC POWER SYSTEM WITH MODULAR SEALED ENCLOSURE

FIELD

The present invention relates generally to electronic power systems for surgical instruments and, more specifically, to reusable electronic power systems enclosed within a sealed enclosure capable of enduring a sterilization process.

BACKGROUND

Within an operating room (OR) or other clinical environments, maintaining a sterile field for patients is of paramount importance. As one skilled in the art will appreciate, the sterile field is a designated area within the OR and other applicable clinical environments that is free of microorganisms and/or pathogens that could infect a patient. In the case of invasive procedures on a patient, maintaining the sterile field is essential as to prevent the transmission of microorganisms or pathogens to the patient. To maintain the sterile field, medical professionals employ surgical asepsis, which requires adherence to strict procedures, such as opening and using sterilized instruments that may come into contact with the patient. With current surgical instruments, certain components, specifically power sources and power source enclosures, are incapable of withstanding a sterilization process after use due to their non-modular nature. Resultantly, medical professionals often use several single use components, thereby resulting in excessive waste.

One way to reduce waste from single use components is to utilize components which can be sterilized according to the requirements of the sterile field. A problem with battery powered equipment is that existing batteries cannot withstand certain sterilization processes, such as steam sterilization. Sterilization processes and devices, such as steam sterilization via steam autoclaves, require a combination of temperatures ranges and pressures between 120-132 degrees Celsius and 15-30 pound force per square inch (psi) respectively. These ranges far exceed the tolerances of most commercial off the shelf (COTS) batteries, making the use of batteries less than ideal when used in a sterile operation. Some batteries can be sterilized using ethylene oxide, however, that process is time consuming, taking 8-10 hours and typically not available in a hospital setting.

Thus, there still exists a need for power systems capable of powering surgical devices and undergoing sterilization processes to enable multiple uses within sterile fields of clinical environments. The technology disclosed herein addresses the aforementioned challenges.

SUMMARY

There is provided, in accordance with an example of the present technology, a sterilizable powered electronics system for a surgical instrument that can include a boost regulator circuit, an ultracapacitor, and a sealed enclosure. The boost regulator circuit can be configured to electrically connect to one or more batteries and configured to output at least one of a predetermined voltage or a predetermined current. The ultracapacitor can be electrically connected to the boost regulator circuit. The sealed enclosure can enclose the boost regulator circuit and the ultracapacitor and can be configured to withstand temperatures greater than 50° C. and pressures greater than 15 psi. At least one of the boost regulator circuit or the ultracapacitor can be configured to be electrically connected to an instrument motor. In some embodiments, control electronics, including motor control, processors, and memory can be included in the sealed enclosure and can survive repeated sterilization cycles.

Additional features, functionalities, and applications of the disclosed technology are discussed in more detail herein.

BRIEF DESCRIPTION OF THE DRAWINGS

FIG. 6B is a table of parameters for exemplary sterilization processes; and

DETAILED DESCRIPTION

The following detailed description should be read with reference to the drawings, in which like elements in different drawings are identically numbered. The drawings, which are not necessarily to scale, depict selected examples and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives, and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 70% to 110%.

As used herein, the terms "patient," "host," "user," and "subject" refer to any human or animal subject and are not intended to limit the systems or methods to human use, although use of the subject invention in a human patient represents a preferred embodiment.

As used herein, the term "proximal" indicates a location closer to the operator or physician whereas "distal" indicates a location further away to the operator or physician.

As used herein, the term "steam autoclave" can include a machine, system, mechanism, or device that is capable of removing harmful microorganisms, pathogens, or bacteria via steam under pressure. As one skilled in the art will appreciate, the nomenclature "autoclave" within the healthcare sector is synonymous with "steam sterilizer." In other words, "steam autoclave" with respect to the present disclosure, can be understood to be any machine, system, mechanism, or device that includes a pressure vessel capable of housing items and subjecting them to steam at a predetermined temperature whilst under pressure to eliminate harmful microorganisms and pathogens on said items.

Figure 1:
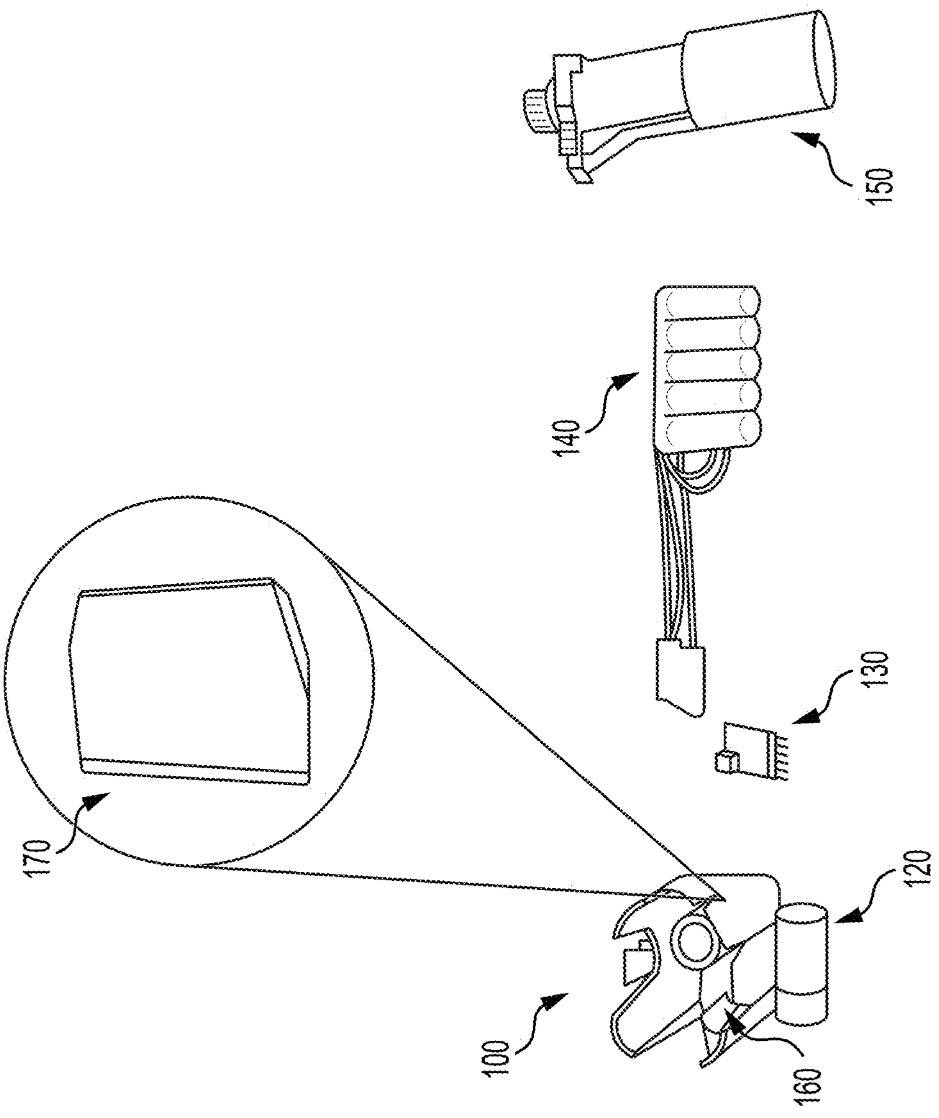
FIG. 1 is an illustration of the components of an exemplary sterilizable powered electronics system, in accordance with an example of the disclosed technology.

FIG. 1 is an illustration of the one or more components of an exemplary sterilizable powered electronics system 100 for a surgical instrument 110 (FIG. 5) such as a surgical stapler. As illustrated in FIG. 1, the sterilizable powered electronics system 100 can include a boost regulator circuit 130, an ultracapacitor (or ultracapacitors) 140, and a sealed enclosure 160. An ultracapacitor (also known as a "supercapacitor") are electrochemical capacitors that have an unusually high energy density when compared to common electrolytic capacitors, typically on the order of thousands of times greater than a high-capacity electrolytic capacitor. An electric (or electrochemical) double layer capacitor ("EDLC") is a common type of ultracapacitor. The ultracapacitor 140 may include multiple capacitors in one package, or may include multiple separately packaged capacitors; however, for the sake of simplicity, the ultracapacitor 140 will be referred to herein in singular form.

In some examples, the ultracapacitor 140 and the boost regulator circuit 130 can be sealed in the sealed enclosure 160, and the resulting assembly can be subjected to steam sterilization and reused on multiple patients. The sealed enclosure 160 can include one or more electrical connectors configured to mate with a surgical instrument 110 to provide power to the surgical instrument 110. The boost regulator circuit 130 is configured to provide a steady voltage output to the surgical instrument 110, and the ultracapacitor 140 is configured to provide instantaneous current required by the surgical instrument 110. The sealed enclosure 160 can further include one or more electrical connectors configured to receive electrical power from one or more batteries 120. The ultracapacitor 140 can be configured to be recharged by the one or more batteries 120. An advantage of the powered electronics system 100 is that it can deliver the required electrical current to the surgical instrument 110 without relying on the one or more batteries 120 to deliver the instantaneous power and/or current. In many prior powered surgical device applications which rely on the battery to provide required instantaneous current, the battery energy is overpowered, meaning that a battery retains a large portion of its charge at the end of a procedure, and this energy is wasted. In some examples, the sterilizable powered electronics system 100 can allow for a battery selection that is sufficient to meet the total power usage requirements, thereby reducing battery size and energy waste compared to at least some prior systems.

The boost regulator circuit 130, as shown in FIG. 1, can be configured to electrically connect to one or more batteries 120. As known in the art, the role of the boost regulator circuit 130, also known as DC-DC converters and boost circuits, is to step-up an input voltage to a higher output voltage as required by a load. A boost regulator circuit 130 can include components such as a switch, an inductor, a capacitor, and a diode to increase an input voltage to a higher output voltage as required by the load. As a result of the increase in voltage realized at the output of the boost regulator circuit 130, there is also a decrease in current supplied to the load. The tradeoff between an increase in voltage and decrease in current due to the boost regulator circuit 130 can be attributed to the conservation of energy axiom. In other words, by the axiom of conservation of energy, the power exiting the boost regulator circuit 130 (Pout) must equal the power entering the boost regulator circuit 130 (Pin). Alternatively, other DC-DC converters or regulators can be used as understood by a person skilled in the art, and the circuit 130 need not necessarily be a "boost regulator" type converter/regulator. For the sake of simplicity of discussion, circuit 130 is referred to herein as a "boost regulator circuit"; however, the disclosure is not limited to one particular converter or regulator configuration.

With respect to the present disclosure, power at the input to the boost regulator circuit 130 is calculated by multiplying an input current ($I_{in}$) by an input voltage ($V_{in}$). Similarly, the output power of the boost regulator circuit is calculated by multiplying an output current ($I_{out}$) by an output voltage ($V_{out}$). Resultantly, by applying the axiom of the conservation of energy, using the boost regulator circuit 130 to step up the input voltage to the output voltage seen at the load results in less available current at the output of the boost regulator circuit 130 in comparison to the input current to the boost regulator circuit 130. In this way, the boost regulator circuit 130 can perform the functions of "boosting" electrical power produced by the one or more batteries 120 of the system 100 and "regulating" electrical power draw from the batteries 120. Alternatively, the circuit 130 can "step-down", or otherwise regulate electrical voltage from the one or more batteries as understood by a person skilled in the pertinent art.

As mentioned previously, the boost regulator circuit 130 can be electrically connected to the one or more batteries 120 which provide a direct current (DC) power source to the boost regulator circuit 130. The one or more batteries 120 can be configured to output at least one of a predetermined voltage or a predetermined current. As one skilled in the art will appreciate, batteries are devices that contain one or more electrochemical cells, wherein the one or more electrochemical cells are capable of converting chemical energy into electrical energy. Various factors such as chemical reactions within the electrochemical cells, concentrations of components that comprise the battery, and polarization of a battery can determine performance metrics of the battery, such as voltage and thereby current. As will also be appreciated, the power system and design parameters of a system or device determines the type of battery utilized as a power source for a specific system or device.

In some embodiments of the present disclosure, the one or more batteries 120 can be single use (e.g. alkaline, lithium, carbon zinc, etc.) or rechargeable (lithium ion, nickel-cadmium, nickel-metal hydride, etc.) and come in several form factors as understood by a person skilled in the pertinent art. Some types of batteries (e.g. nickel-cadmium, nickel-metal hydride) may not be feasible due to government regulations in various legal jurisdictions. In the illustrated example, the one or more batteries 120 includes a CR123a battery. In some examples, the one or more batteries 120 can undergo independent sterilization processes, such as gamma sterilization and the like prior to introducing them into the sterilizable powered electronics system 100. Once independently sterilized, the one or more batteries 120 can be independently aseptically introduced into the sterile field of the clinical environment. In some embodiments, the one or more batteries 120 can be aseptically introduced into the sterile field upon sterilization via the sealed enclosure 160. The one or more batteries 120 need not be capable of withstanding steam sterilization; however, the one or more batteries 120 may be capable of withstanding steam sterilization.

The ultracapacitor 140, as shown in FIG. 1, can be configured to electrically connect to the boost regulator circuit 130. As one skilled in the art will appreciate, capacitors are electronic devices capable of storing and releasing electrons, which results in the charging and discharging of electrical energy. Ultracapacitors store larger quantities of electrical energy and discharge stored energy quicker than standard capacitors, which is due to ultracapacitors storing positive and negative ions in conjunction with liquid electrolytes to transfer energy. With respect to the present disclosure, the ultracapacitor 140 within the present system 100 can be advantageous as it is capable of providing high instantaneous current during heavy firing of the surgical instrument 110. The ultracapacitor 104, in combination with the boost regulator circuit 130 significantly reduces voltage sag during heavy firing of the surgical instrument 110 compared to using a battery alone. In other words, the ultracapacitor 140 and boost regulator circuit 130, while being used in a surgical instrument 110, such as a surgical stapler, can prevent electric energy from dipping while the surgical stapler is in use. Between uses, the one or more batteries 120 can deliver energy via the boost regulator circuit 130 to charge the ultracapacitor 140. The ultracapacitor 140, within the sterilizable powered electronics system 100, is also advantageous due to high temperature tolerances, which can allow the ultracapacitor 140 to independently withstand the steam sterilization processes within steam autoclaves. For example, commercially available ultracapacitors have thermal tolerances of 125° C., making them capable of withstanding sterilization processes such as steam sterilization within steam autoclave and the like.

The battery 210 may be underpowered for driving the motor by itself, without the ultracapacitor 140 in the system. For instance, the battery can have a high internal resistance (e.g. around 300 mΩ), such that when the motor demands high power from the battery (and thereby high current), the voltage output from the battery lowers due to voltage drop across the internal resistance. With the ultracapacitor 140 in the system, the battery can be more slowly discharged to maximize the battery voltage, i.e., reduce wasted energy due to heating of the internal battery resistance. Once the ultracapacitor 140 is charged by the battery 210, the system now has the ability to command a high current from the ultracapacitor 140 and deliver the stored energy without a voltage drop. For instance, a system in which the motor requires 5 A, but for the ultracapacitor, the voltage at the output of the battery 210 may fall from 3.2 V (nomial) to 1.5 V, which, as a result provides only 7.5 W to the motor. With the ultracapacitor 140, this example system is capable of providing 5 A at a 3.2 V, thereby providing 16 watts to the motor.

As one skilled in the art will appreciate, capacitors can have operational and storage temperatures and pressures much higher than any battery can handle. This is due in part to the fact that capacitors do not need the venting protection batteries have, which can allow capacitors to experience temperatures well above 120° C. for limited amounts of time. In the case of surgical staplers, such as the Echelon 3000 Endocutter, a 2 Farad (F) ultracapacitor along with the device electronics, which can include processors and memory, with a sealed enclosure taken repeatedly through a steam sterilization process can continue to operate as desired after returning to normal operating conditions post sterilization. The high temperature and pressure tolerances of the ultracapacitor 140 can allow the system 100 to be "flash sterilized" or fully undergo normal steam sterilization processes. In other words, the system 100 can be configured to endure a shorter and cooler steam sterilization process or undergo the normal full steam sterilization cycle while maintaining normal operability.

In some embodiments, the sealed enclosure may be coupled to gamma sterilized CR123a primary cells, being independently introduced aseptically in the operating room (OR). In short, the surgical instrument 110 the one or more batteries 120, and the device electronics 150 can be fully sterile, requiring no special handling or use. Once the practitioner finishes using the surgical instrument 110, the one or more batteries 120 can be disposed of in an appropriate battery waste stream and the device electronics can be cleaned and sent for re-sterilization. It should be appreciated that in the OR, specifically in the European Union (EU), there are separate waste streams for batteries, electronics and normal metal and plastic portions. With respect to the present disclosure, the system 100 can conform to the waste regulations within the EU while reducing the amount of battery waste, which can make the system 100 much more sustainable.

In some embodiments of the present disclosure, the ultracapacitor 140 can have operational parameters of approximately 9V to 20V at a capacitance of 2 F to 20 F. In one example, the ultracapacitor 140 has a voltage rating of 13.5V and a capacitance of 2 F. In one specific example, the 2 F ultracapacitor 140 can be capable of successively firing a surgical instrument 110, such as the Echelon™ line of staplers or comparable powered surgical staplers. For instance, the Echelon™ 3000 Endocutter utilizes a 12V instrument motor 154 at 7 A, which can produce the maximum 200 lbs of firing force needed in overstress condition two (2) full times over a firing distance of 60 mm. When the surgical stapler is in use, there can be approximately 15-30 s between firings to around 2-3 min between firings, wherein each of the time ranges considers how long it takes to reload and reposition the stapler. In other words, to allow the surgical stapler to be successively fired and considering the minimum reload time, the capacity of the ultracapacitor can be configured to be above the minimum threshold of 1 F. In this scenario, the ultracapacitor 140 can require between 10-15 s to recharge if it were given infinite draw at the expected voltage utilizing a four cell battery.

In an embodiment that utilizes a one-cell battery, the ultracapacitor 140 can take approximately 40-60 s to recharge after a full overstress firing. Therefore, a viable range of capacities can be 1.1 F-4 F.

In the case of a system that has the separation between the one or more batteries 120 to the ultracapacitor 140 and the ultracapacitor 140 to the device electronics, a viable range of capacitances can approximately 1.8 F-2.2 F. Alternatively, if the system 100 electrically resembles the schematic in FIG. 2, the one or more batteries 120 and ultracapacitor 140 can simultaneously provide electrical power to the device electronics, which can allow the ultracapacitor to be configured with a capacitance of 0.8 F for a one cell system and 0.5 F for a two cell system.

In one example, if the one or more batteries contain four cells, it could be sized as small as 0.25 F due to the one or more batteries 120 being capable of powering the system 100.

Regardless of the number of battery cells, the ultracapacitor can be configured to prevent voltage sag as the instrument motor 154 draws heavy current.

The aforementioned capacitances ranges can be derived by Echelon™ line of staplers or comparable powered surgical staplers. For instance, the system can be configured to utilize four (4) CR123a lithium primary batteries. Using a single 3V cell to power a 12V motor 154 with the current draws discussed in the present disclosure may be understood relatively to a CR123a primary cell. In some embodiments, rechargeable CR123a batteries can be used realize increased sustainability of the system 100. However, it should be appreciated that rechargeable CR123a batteries may have differing power capacities and/or differing voltage sag under load conditions, which can require more or less cells to allow for operability of the system 100. Although the present disclosure contemplates CR123a batteries, it should be appreciated that other cells can be used. In alternate embodiments where other cells are used, additional cells may be required to balance the time power requirements for the system 100.

While the foregoing examples are directed primarily to the Echelon™ line of staplers, the specific values of parameters such as voltage, capacitance, power, current, charge times, firing times, etc. can be determined for other surgical staplers and surgical instruments as understood by a person skilled in the pertinent art by applying the concepts presented herein.

As known in the art, the energy which can be stored in a capacitor is dependent on the capacitance and voltage rating of the capacitor. As such, design consideration for the system 100 can be adjusted to increase or decrease the capacitance and/or voltage based on the amount of current or electric potential needing to be distributed to a load as understood by a person skilled in the pertinent art. The ultracapacitor 140 can include multiple capacitor cells connected in series or parallel by a printed circuit board to achieve the desired voltage rating and capacitance and provide protection and/or regulation of the multiple capacitor cells. In some embodiments, the ultracapacitor 140 can have dimensional parameters of approximately 2.0"×0.45"×1.3". As will be appreciated, the dimensional parameters of the ultracapacitor 140 can be adjusted to conform to the system 100 requirements. In some embodiments, the ultracapacitor 140, as shown in FIG. 1, can be enveloped in a heat shrink material, which can protect the ultracapacitor 140 from dust, moisture, and other environmental forces that can damage the component.

The voltage requirements of the ultracapacitor 140 can be understood to be dependent on windings of the instrument motor 154. In some embodiments, the system 100 may power a 6V instrument motor 154 or a 12V instrument motor 154 within a surgical instrument 110, such as one of the Echelon™ line of staplers or comparable powered surgical staplers. Mechanically, the 6V motor 154 can be understood to have similar torque curve characteristics to the 12V motor 154. Although the general work required to move an I-beam of the surgical stapler 60 mm with 200 lbs force is the same for both motors, the difference in voltage can require the system 100 to provide the 6V motor 154 with at least double the current to achieve the same work as the 12V motor 154.

In other words, a viable range of voltage ratings for the ultracapacitor 140 can be approximately 6V-24V. For example, the voltage ratings for the ultracapacitor can be 12V, which in part can be based on design considerations such as the size of the motor, weight of the motor, cost of the motor, efficiency of the motor, and electrical current capacity of the wiring and device electronics. In some embodiments, the instrument motor 154 may be a 12V instrument motor 154 and the surgical stapler may have device electronics 150 that may operate at 7 A. Given that the device electronics 150 can be configured to run at approximately 3-6V, the device electronics 150 may not require high current draw from the ultracapacitor 140 except when the instrument motor 154 begins to operate. Resultantly, the ultracapacitor 140 having a 12V voltage rating and 2 F capacitance and given sufficient time to charge from the one or more batteries 120, can be configured to discharge the needed electrical power to the system 100 and device electronics 150 which can include the instrument motor 154.

The sealed enclosure 160, as shown in FIG. 1, can be configured to enclose the boost regulator circuit 130 and the ultracapacitor 140. In some embodiments, the sealed enclosure can be a three dimensional (3D) printed enclosure. As one skilled in the art will appreciate, 3D printing is the construction of a 3D object from a computer aided design (CAD) model or a digital CAD model. With respect to the present disclosure, the sealed enclosure 160, as a 3D printed enclosure, can be configured to conform to a desired form factor that can enclose the one or more batteries 120, boost regulator circuit 130, and the ultracapacitor 140. Additionally, or alternatively, the enclosure can be manufactured by other suitable means, such as extrusion, molding, etc. as understood by a person skilled in the art. The sealed enclosure 160 can be advantageous in the sterilizable powered electronics system 100 as it can be placed within a steam autoclave to undergo a steam sterilization process. In some embodiments, the sealed enclosure 160 can include a thermal mass member 170 that can be configured to minimize the overall internal temperature of the components within the sealed enclosure 160, as shown in FIG. 1

As one skilled in the art will appreciate, thermal masses are understood as materials that have the ability to absorb, store, and release heat. With respect to the present disclosure, the thermal mass member 170 can be a ceramic plate or another suitable material that can be configured with a high thermal absorption capacity to reduce the temperature within the sealed enclosure 160 beneath the ambient temperature within a steam autoclave during the steam sterilization process. In some embodiments, the sealed enclosure 160 can include at least one of an ultrasonic seal or a gasket seal, which can be configured to prevent the ingress of moisture into the sealed enclosure 160 whilst maintaining a temperature within the sealed enclosure 160 lower than an ambient temperature of the steam autoclave during the steam sterilization process.

Figure 2:
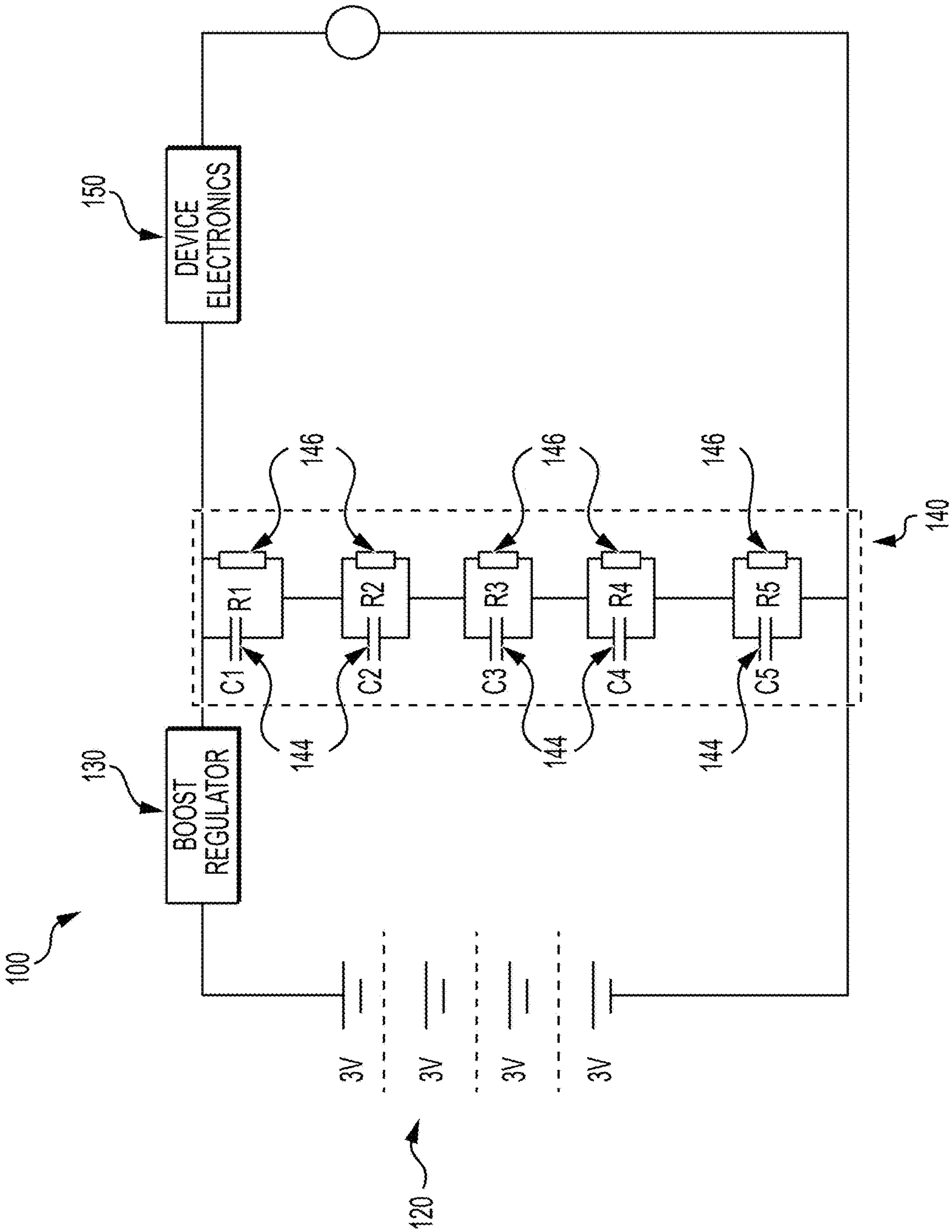
FIG. 2 is a circuit schematic for an exemplary sterilizable powered electronics system, in accordance with an example of the disclosed technology.

FIG. 2 is a circuit schematic for an exemplary sterilizable powered electronics system 100. As shown in FIG. 2, each of the one or more batteries 120 are connected in series to the boost regulator circuit 130. The one or more batteries 120 can be configured to output a current of approximately 1.5-10 amperes (A) to the boost regulator circuit 130. The one or more batteries 120 can also be configured to output a voltage of approximately 3.1V-12V. As known in the art, direct current (DC) power sources, such as the one or more batteries 120 of the present disclosure, may not be ideal power sources. In other words, the one or more batteries 120 of the present disclosure, which are a type of DC power source, can provide approximately more or less than the rated voltage indicated on their packaging when introduced into a circuit.

The one or more batteries 120 and boost regulator circuit 130, as shown in FIG. 2, are connected in series to the ultracapacitor 140. The electrical schematic for the ultracapacitor 140 shown in FIG. 2 is an illustration of one potential configuration of the ultracapacitor 140. As illustrated, the ultracapacitor 140, includes five capacitor cells 144 electrically connected in parallel with one or more resistors 146. Capacitor cells 144 cannot change voltage instantaneously, and the resistors 146 provide a shunt to route current to have controlled dynamic charge and discharge of the capacitor cells 144. The five resistor 146/capacitor cell 144 combinations are connected in series. The ultracapacitor 140 may be better suited to survive steam sterilization in a non-energized state. The resistors 146 can further function to discharge the capacitor cells 144 when the one or more batteries 120 are disconnected from the circuit.

As also known in the art, the arrangement of capacitors in series and parallel combinations impacts the behavior of the element within a circuit. As illustrated, each capacitor cell 144 has a voltage rating of 2.7V and a capacitance of 10 F so that the resultant series arrangement of capacitor cells 144 has a voltage rating of 13.5V and 2 F. Alternatively, the one or more capacitor cells 144 can be arranged in parallel to increase capacitance. The larger the capacitance of a capacitor or the combination thereof multiple capacitors, for a given voltage rating, the larger the amount of electrical energy capable of being stored in the single capacitor or the combination thereof multiple capacitors. In other words, a capacitor having a 2 F capacitance would store less electrical energy than a capacitor with the same voltage rating having a 50 F capacitance. In contrast to the parallel arrangement of capacitors, connecting capacitors in series results in the combination of capacitor cells 144 having increased voltage rating with decreased capacitance. As understood by a person skilled in the art, the capacitor cells 144 of the ultracapacitor 140 can be arranged in parallel and/or series, and with the appropriate shunt resistors 146 to deliver current required by the surgical instrument 110 between recharging intervals, to match the voltage requirements of the surgical instrument 110 and output of the boost regulator circuit 130.

As shown in FIG. 2, the ultracapacitor 140 can be connected in series with the boost regulator circuit 130 and thereby the one or more batteries 120. In some embodiments, at least one of the boost regulator circuit 130 or the ultracapacitor 140 can be electrically connected to device electronics 150 that can include an instrument motor 154. The surgical instrument 110, such as a surgical stapler, can include device electronics like the instrument motor 154, which can be configured to electrically connected to the boost regulator circuit 130 and the ultracapacitor 140.

In some embodiments, the boost regulator 130 and capacitor 140 can be encapsulated in enclosure 160 (FIG. 1) for sterilization. In some embodiments, the device electronics 150 can also be encapsulated in enclosure 160. Portions of the exemplary sterilizable powered electronics system 100 not encapsulated in the enclosure 160 can be electrically coupled to the enclosure 160 via connectors and/or can be electrically coupled to electronics within the enclosure 160 via wires extending through sealed openings of the enclosure 160.

In some embodiments, the electrical power requirements for operation of a surgical stapler can be understood to be related to the motor windings. For example, a 6V motor can have a similar operation torque curve to a 12V motor. In other words, the general work of the system 100 to move the I-beam of a surgical stapler 60 mm with 200 lbs force is the same for a 6V motor or the 12V motor. However, in the case of utilizing a 6V motor, the surgical instrument 110 may require additional current to get the same work that is realized with the 12V motor. In some embodiments, the power output for an exemplary sterilizable powered electronics system 100 in accordance with the present disclosure can between 6V-24V for a 12V motor used in a surgical stapler. The aforementioned voltage range for the exemplary sterilizable powered electronics system 100 can be understood to be based on the size, weight, cost, efficiency of the motor as well as the electrical current capacity of the wiring and control electronics. In some embodiments, an exemplary configuration for a surgical instrument 110 can include device electronics 150 and a 12V motor 154 that can be configured to run at 7 A. In said exemplary configuration, the system 100 can also include the boost circuit 130 and 2 F ultracapacitor 140, which can be configured to be charged with the voltage needed to operate the surgical stapler. In most instances, the device electronics 150 can require less voltage, typically around 3-6V, and thereby not require high current draw. In some instances however, high current draw from the device electronics 150 can occur specifically from a motor control circuit 152 that can be configured to accommodate and control operation of the motor 154 for the surgical stapler.

Figure 3:
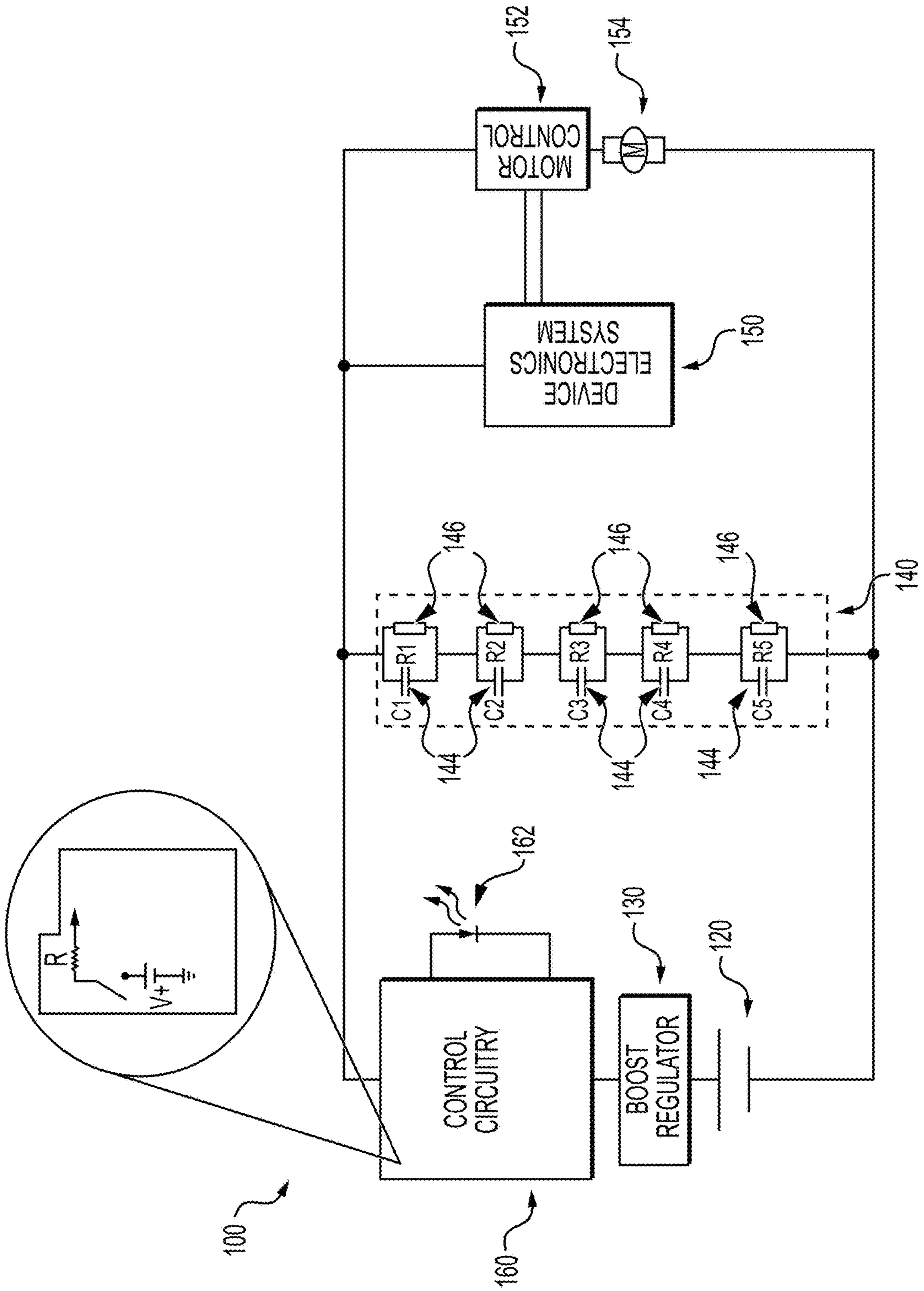
FIG. 3 is an alternate embodiment of a circuit schematic for an exemplary sterilizable powered electronics system, in accordance with an example of the disclosed technology.

FIG. 3 is an alternate embodiment of a circuit schematic for an exemplary sterilizable powered electronics system 100. In said alternate embodiment, the ultracapacitor 140 can be electrically switchable, which can allow the ultracapacitor 140 to charge from the one or more batteries 120 or power the device electronics 150 using control circuitry 160. The control circuitry 160 can include a mechanical or electrical switch (e.g., relay, transistor, etc.) which can be closed to make electrical connection to the circuit or opened to decouple the boost regulator 130 and battery 120 from the remainder of the circuit and may include additional elements to regulate voltage and/or current (e.g., resistor). The switch can function as a simple on-off switch or can have pulse width modulation capabilities. The arrangement as shown in FIG. 3 can be advantageous as it allows the device electronics 150 to have the needed power. Furthermore, when the instrument motor 154 engages and draws substantial electrical power upon receiving a signal from the motor control circuit 152, the use of the control circuitry 160 as shown in FIG. 3 protects high instantaneous draw directly from the one or more batteries 120. High instantaneous draw from the one or more batteries 120 can trip the internal thermal limiter due to too much power being drawn too fast. Resultantly, the control circuitry 160 in the present arrangement shown in FIG. 3 can be understood to control electrical power draw from the batteries 120, thus keeping batteries 120 from reaching their respective thermal limit.

In some embodiments, the boost regulator 130 and capacitor 140 can be encapsulated in enclosure 160 (FIG. 1) for sterilization. In some embodiments, the device electronics 150 can also be encapsulated in enclosure 160. In some embodiments, the motor control 152 can also be encapsulated in enclosure 160. In some embodiments, the control circuitry 160 can also be encapsulated in enclosure 160. Portions of the exemplary sterilizable powered electronics system 100 not encapsulated in the enclosure 160 can be electrically coupled to the enclosure 160 via connectors and/or can be electrically coupled to electronics within the enclosure 160 via wires extending through sealed openings of the enclosure 160.

Figure 4:
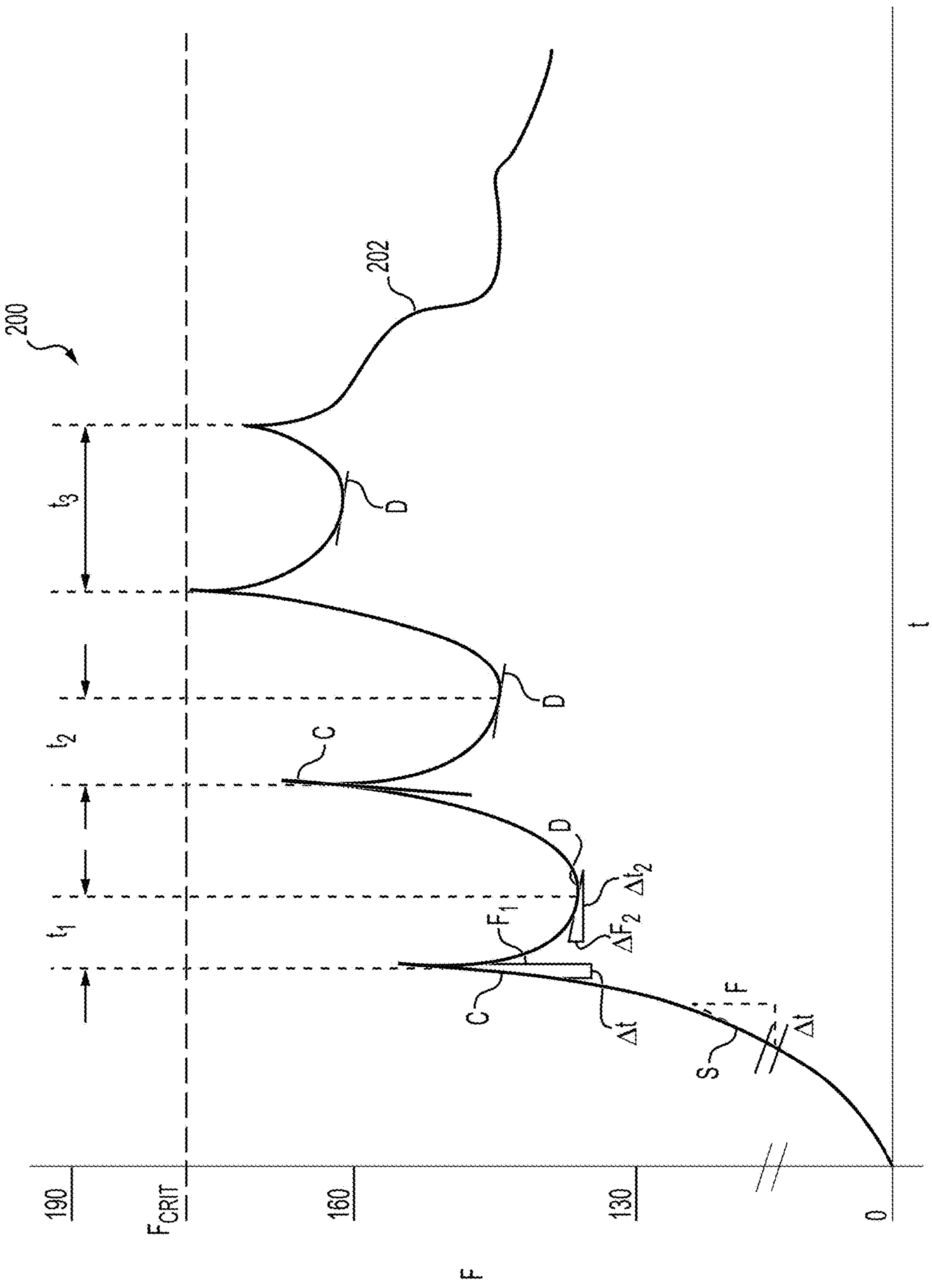
FIG. 4 is an example graph showing a curve representative of a closing force signal over time for various aspects of a surgical instrument powered by an exemplary sterilizable powered electronics system.

FIG. 4 is an example graph 200 showing a curve 202 representative of a closing force signal over time for closure of an end effector of a surgical instrument 110 (FIG. 6) powered by an exemplary sterilizable powered electronics system 100 (FIGS. 1-3). FIG. 4 is adapted from FIG. 108 of U.S. Pat. No. 10,357,247, incorporated by reference as if set forth herein in its entirety. FIG. 4 is provided as an example of forces that the system 100 can provide during operation when powered by the ultracapacitor 140. The exemplary sterilizable powered electronics system 100 (FIGS. 1-3) can include additional aspects disclosed in U.S. Pat. No. 10,357,247; specifically, the exemplary sterilizable powered electronics system 100 can be configured to provide other force profiles experienced during clamping and/or firing disclosed in U.S. Pat. No. 10,357,247 when powered by the ultracapacitors 140. The force profiles provided in U.S. Pat. No. 10,357,247 are illustrative examples, and the exemplary sterilizable powered electronics system 100 can be configured to provide alternative force profiles as understood by a person skilled in the pertinent art. In some embodiments, the exemplary surgical system 100 can provide such forces during clamping and/or firing time periods without drawing power from the one or more batteries 120.

The closing force F is shown along the vertical axis and the time t is shown along the horizontal axis. The closing force F represented on the vertical axis can be a force experienced by tissue clamped between the jaws of the surgical stapler, a force experienced by the jaws of the surgical stapler, a force experienced by a closure tube of the surgical instrument, and/or any combinations thereof. The closing force F can be measured in any suitable manner, either directly or indirectly. For example, according to various aspects, the closing force F can be measured directly by a sensor (e.g., a strain gauge) positioned on the anvil, on the elongated channel, on the closure tube, or indirectly by an impedance of the tissue, a current draw of the motor, and/or any combinations thereof.

In some embodiments, the change in the closing force F over time t (i.e., the rate of change of the closing force F) may provide useful feedback to the device electronics 150, such as the motor control circuit 152, to control the jaw closing mechanism of the surgical instrument 110. The change in the closing force F over time t may be represented as a derivative of the curve 202 and may be approximated over short periods of time by the equation Slope $S=\Delta F/\Delta t$, where $\Delta F$ is the change of the closing force F and $\Delta t$ is the change of the time t. The value of the slope $C=\Delta F1/\Delta t1$ (a positive value) shown in FIG. 4 may be determined by the device electronics 150 and may represent the first predetermined threshold. Similarly, the value of the slope $D=\Delta F2/\Delta t2$ (a negative value) shown in FIG. 4 may be determined by the device electronics 150 and may represent the second predetermined threshold. Thus, according to various aspects, an algorithm, utilizing the graph 200 shown in FIG. 4, can control the operation of the device electronics based on the determined slope, whether instantaneous or approximated. Resultantly, the sterilizable powered electronics system 100 of the present disclosure can be configured to initiate said closing force F over a time T and firing of the surgical stapler during operation, aided at least in part by the abovementioned algorithm.

Figure 5:
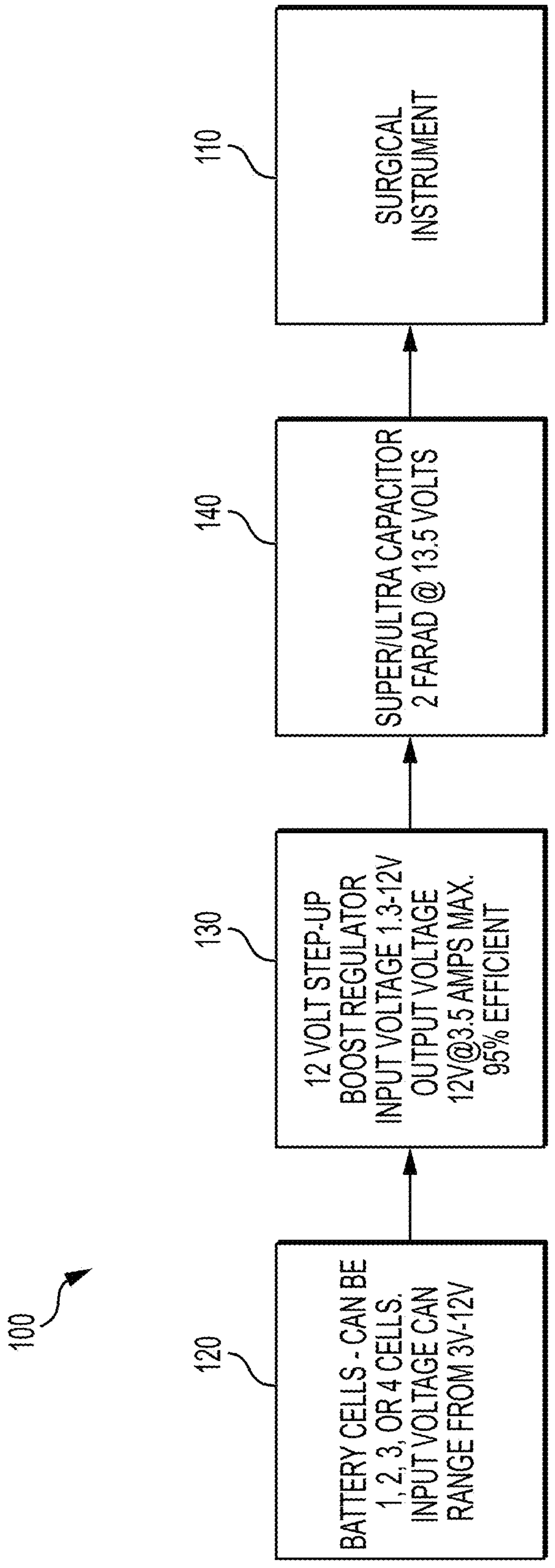
FIG. 5 is an exemplary block diagram for an exemplary sterilizable powered electronics system, in accordance with an example of the disclosed technology.

FIG. 5 is an exemplary block diagram for an exemplary sterilizable powered electronics system 100. As shown in FIG. 5, the one or more batteries 120 can include at least one or more battery cells and can provide an approximate range of input voltages from 3V to 12V. In some embodiments, the boost regulator circuit 130 can accept an approximate range of input voltages from 1.3V-12V and input currents of 1.5 A-10 A. As shown in FIG. 5, the input voltage to the boost regulator circuit 130 can be supplied by the one or more batteries 120, which can be electrically connected in series to the boost regulator circuit 130. As mentioned previously, the ultracapacitor 140 can store and discharge electrical energy from the boost regulator circuit 130 to prevent voltage from dipping while the surgical instrument 110, such as a surgical stapler, is in use under heavy load conditions. Resultantly, the ultracapacitor 140, upon discharging its stored electric energy to the instrument motor 154 while in use, can prevent additional power draw from the one or more batteries 120.

In the case of a surgical stapler, for example, the ultracapacitor 140 can have a sufficient voltage rating and capacitance such that the ultracapacitor 140 can allow the surgical stapler to fire two full times without requiring a recharge of the ultracapacitor 140 by the one or more batteries 120. The recharge time of the ultracapacitor 140 can be shorter than a typical time between two firing strokes. Configured as such, the ultracapacitor 140 is rated with sufficient margin so that the ultracapacitor 140 can reliably deliver energy for each firing stroke of a procedure. Utilizing the stored energy of the ultracapacitor 140 in lieu of solely using the one or more batteries 120 can minimize stalls from the instrument motor 154 when the surgical instrument 110 is placed under heavy loading conditions. In other words, discharging the ultracapacitor 140 while the surgical stapler is in use can enable the surgical stapler to maintain or even increase the output to components, such as the instrument motor 154, when encountering varying load conditions like varying tissue thickness. In some examples, the surgical instrument 110 includes a surgical stapler, or a portion thereof, such as a handle. The surgical instrument 110 includes motor 154 (FIG. 3) configured to be driven by an assembly which includes the one or more batteries 120, boost regulator circuit 130, and ultracapacitor 140, such as the system 100 illustrated in FIG. 1. In one example, the system (FIG. 1) is configured with a form factor similar to an existing battery pack for a surgical stapler such as a battery pack for a powered linear surgical stapler or powered circular surgical stapler from the Echelon™ line of staplers or comparable powered surgical stapler. Alternatively, the sealed enclosure 160, including the boost regulator circuit 130 and ultracapacitor 140 contained therein, can be integral to the handle of the surgical instrument 110. Other electronics, such as the motor 154 may also be protected within the sealed enclosure 160 so that the entire handle can undergo steam sterilization and be reused.

In some embodiments, the form factor of the present system 100 considers the challenges of current medical devices. For example, handheld devices like surgical staplers may have ergonomic limits to their grip spans of controls, weight, and balance given that surgeons have to hold them for significant time. Given that the system 100 can be configured to have components that are both reusable and re-sterilizable, surgeons and clinical environments can realize advantages such as reduced device weight, cost-effective devices, and reduced disposal cost at the conclusion of procedures. Furthermore, in locations such as the EU that may require specific waste disposal streams, the system 100 can conform to applicable disposal regulations thus promoting increased ecological impacts.

In some embodiments, the sealed enclosure 160 may also include an electrical connection that can bridge the contents of the inside of the sealed enclosure 160 to the outside of the sealed enclosure 160. The electrical connection can be overmolded to walls of the sealed enclosure 160, thereby allowing power from the one or more batteries 120 to be routed to the instrument motor 154 and ancillary device electronics. In some embodiments, the sealed enclosure 160 can include, but not be limited to, materials from the groups of plastics and plastic metal hybrids. Examples can include Ultem (Polyetherimide), PEEK (Polyether Ether Ketone), PTFE (Polyamide-imide), HDPE, PI, PAI, PPS, PEI, PES, PPSU, PEKK, PEK, LCP, ETFE, FEP, PFA, PBI, and the like. In some embodiments, the sealed enclosure can be configured to hold its shape under high temperature while shielding the boost regulator circuit 130, ultracapacitor 140, and one or more batteries 120 from direct exposure to high temperatures and pressures.

Figure 6A:
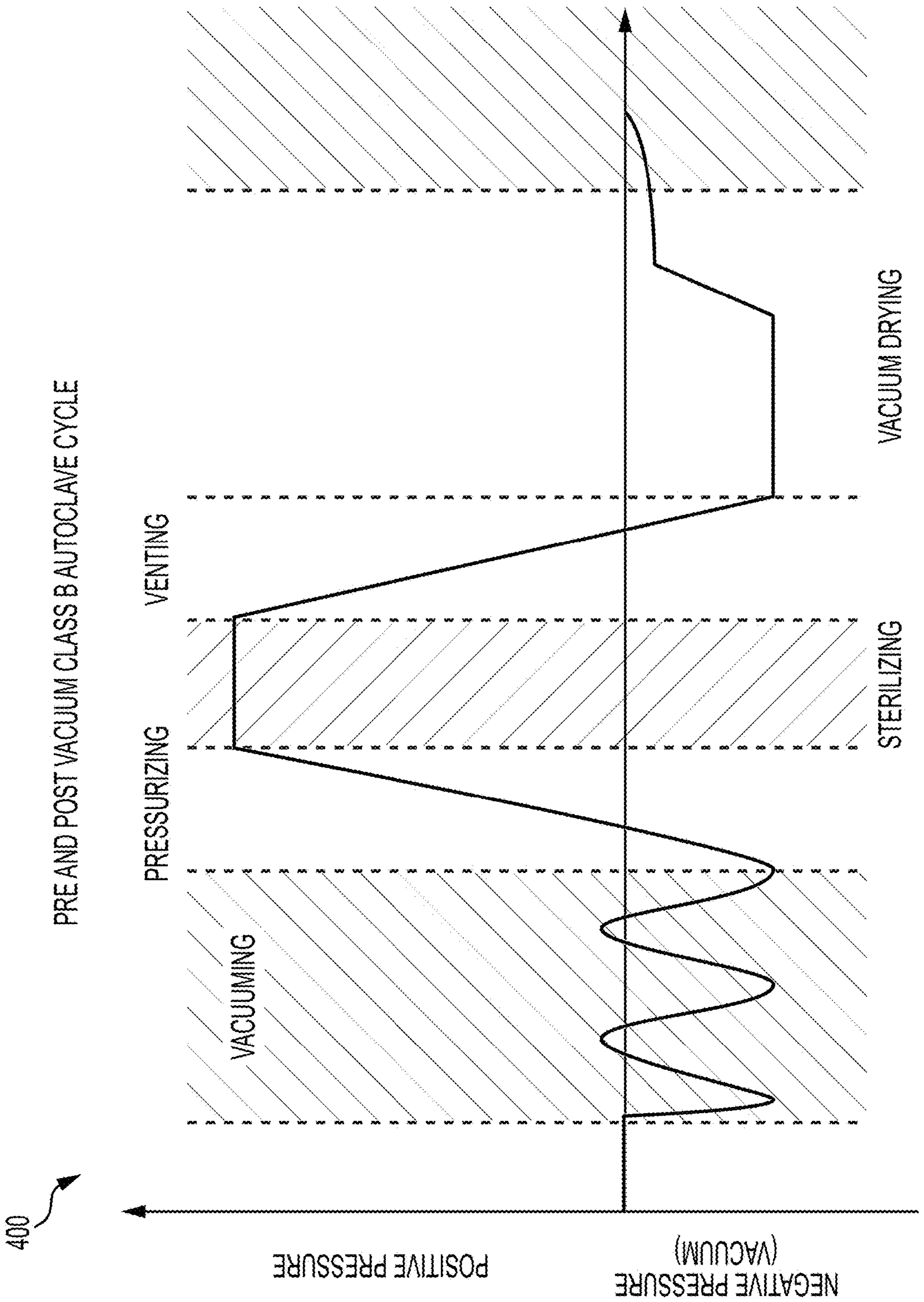
FIG. 6A is a plot of pressure over time for an exemplary steam sterilization process.
Figure 6C:
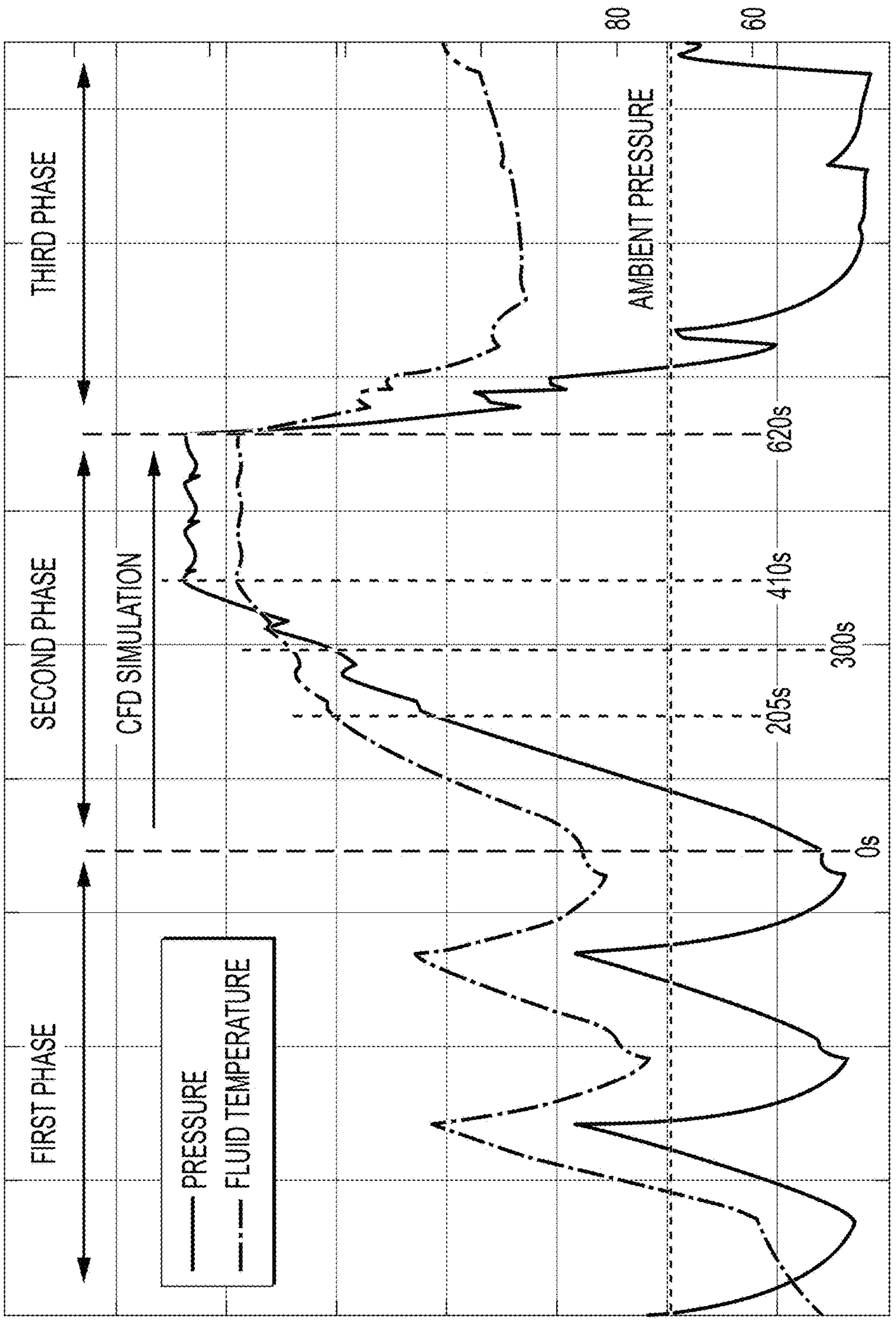
FIG. 6C is a diagram for exemplary steam sterilization process parameters.

FIGS. 6A-6C are diagrams detailing various parameters and features of exemplary sterilization processes. In some embodiments, the pressure of the steam autoclave can fluctuate between positive and negative pressures during various phases of the steam sterilization, as illustrated in the plot 400 shown in FIG. 6A. As shown in FIG. 6B, the steam autoclave, during steam sterilization process, can create ambient temperatures and pressures within an approximate range of 121° C.-132° C. and 15-30 psi, respectively. It should be appreciated that the time that an item is subjected to the temperatures and pressures, indicated in FIG. 6B, can depend on the manner in which items are packaged within the steam autoclave. Although the technology of the present disclosure, for exemplary purposes, contemplates steam sterilization via the steam autoclave, it should also be appreciated that the present disclosure is not so limited with respect to sterilization processes. In other words, other types of sterilization processes, such as chemical vapor, dry heat wrapped, ethylene oxide, and the like can be used with the present technology.

FIG. 6C shows an exemplary steam sterilization cycle for a steam autoclave, in accordance with the present disclosure, that the sealed enclosure 160 can be configured to withstand. As shown in FIG. 6C, the fluid temperature and pressure, with respect to an ambient pressure, can periodically rise and fall throughout the first phase. During the second phase of the exemplary steam sterilization cycle, the fluid temperature and pressure, which can be illustrated utilizing the computational fluid dynamics (CFD) simulation shown in FIG. 6C, can exponentially increase reaching their highest levels with respect to the ambient temperature and the first and third phases. During the third phase, both the fluid temperature and the pressure, as shown in FIG. 6C, can decrease from their peak levels observed in the second phase and maintain levels close to the first phase with respect to the ambient pressure. In some embodiments, the sealed enclosure 160 can be configured to withstand temperature ranges of approximately 121° C.-132° C. and pressure ranges of approximately 15-30 psi.

In relation to the sterilization options for the sealed enclosure 160, sealed enclosure 160 can be designed to withstand temperatures in the range of approximately 50° C. to 121° C.; from 50° C. to 132° C.; ranges up to 50° C. to 170° C.; and 121° C. to 132° C. Pressures can range from approximately atmospheric to 15 psi; from atmospheric to 30 psi, and from atmospheric to 40 psi. The sealed enclosure 160 can withstand ranges of temperature and/or pressure from time ranging from approximately a few minutes to hours. Time durations of approximately 0-3 minutes, 0-8 minutes, 0-10 minutes 0-15 minutes, 0-20 minutes, 0-60 minutes, and then approximately 3-8, 3-10, 3-15, 3-20 and 3-60 minutes are also contemplated.

In some embodiments, the sealed enclosure 160, can be configured to withstand a temperature of 121° C. at 15 psi for 15 minutes, while temperatures between approximately 121° C. and 132° C. at 30 psi for times ranging from approximately 3 to 10 minutes. Other ranges include a pressure of 15 psi for at least 15 minutes and a pressure of 30 psi for greater than 3 minutes. The sealed enclosure 160 can prevent fluid ingress into an interior portion of the sealed enclosure 160 while being exposed to these temperatures and pressures, thereby inhibiting fluid from reaching the boost regulator circuit 130 and the ultracapacitor 140 during steam sterilization. For instance, the sealed enclosure 160 can include a perimeter which is ultrasonically sealed or gasket sealed. Through using ultrasonic seals or gasket seals on the scaled enclosure 160, the sealed enclosure 160 can further shield the boost regulator circuit 130 and the ultracapacitor 140 from experiencing the peak temperatures and/or pressures of the environment outside of the sealed enclosure 160 during steam sterilization. In some embodiments, the sealed enclosure 160 can include thick or even closed cell portions that can be configured to allow the sealed enclosure 160 to have improved thermal insulative properties to prevent the internal temperature of the sealed enclosure 160 from reaching the ambient temperature of the autoclave. The sealed enclosure 160 can also include the thermal mass member 170, as shown in FIG. 1, to absorb thermal energy and minimize internal temperature of the sealed enclosure 160 during sterilization. Resultantly, the sealed enclosure 160 of the present disclosure and the components within the sealed enclosure 160 can withstand the conditions present during the steam sterilization process within the steam autoclave.

The disclosed technology described herein can be further understood according to the following clauses:

Clause 1: A sterilizable powered electronics system 100 for a surgical instrument 110, comprising: a boost regulator circuit 130 configured to electrically connect to one or more batteries 120 and configured to output at least one of a predetermined voltage or a predetermined current; an ultracapacitor 140 electrically connected to the boost regulator circuit 130; and a sealed enclosure 160 configured to withstand temperatures greater than 50° C. and pressures greater than 15 psi, and enclosing the boost regulator circuit 130 and the ultracapacitor 140, wherein at least one of the boost regulator circuit 130 or the ultracapacitor 140 are configured to be electrically connected to an instrument motor 154.

Clause 2: The system 100 according to Clause 1, wherein the surgical instrument 110 comprises the instrument motor 154 configured to be electrically connected to the boost regulator circuit 130 and the ultracapacitor 140.

Clause 3: The system 100 according to Clause 1 or 2, wherein each of the one or more batteries 120 are sterilized via a gamma sterilization process prior to insertion into the sealed enclosure 160.

Clause 4: The system 100 according to any one of Clauses 1-3, wherein each of the one or more batteries 120 is configured to output a maximum current of 5 amperes (A) to the boost regulator circuit 130.

Clause 5: The system 100 according to Clause 4, wherein each of the one or more batteries 120 is further configured to output an approximate voltage of 3.1V while outputting the maximum current.

Clause 6: The system 100 according to any one of Clauses 1-5, wherein each of the one or more batteries 120 is a disposable CR123a battery.

Clause 7: The system 100 according to any one of Clauses 1-6, wherein the sealed enclosure 160 comprises an ultrasonic seal configured to prevent ingress of moisture into the sealed enclosure 160 during a steam sterilization process.

Clause 8: The system 100 according to Clause 7, wherein the ultrasonic seal is further configured to maintain an internal temperature within the sealed enclosure 160 less than that of an external temperature exterior the sealed enclosure 160 during the steam sterilization process.

Clause 9: The system 100 according to any one of Clauses 1-8, wherein the sealed enclosure 160 comprises a gasket seal configured to prevent ingress of moisture into the sealed enclosure 160 during a steam sterilization process.

Clause 10: The system 100 according to Clause 9, wherein the gasket seal is further configured to maintain an internal temperature within the sealed enclosure 160 that is less than that of an external temperature exterior the sealed enclosure 160 during the steam sterilization process.

Clause 11: The system 100 according to any one of Clauses 1-10, wherein the ultracapacitor 140 comprises one or more capacitor cells 144 electrically connected in parallel with one or more resistors 146, the ultracapacitor 140 electrically connected in series with the boost regulator circuit 130.

Clause 12: The system 100 according to any one of Clauses 1-11, wherein the ultracapacitor 140 is configured to store the predetermined voltage and the predetermined current from the boost regulator circuit 130 as electric potential energy for the surgical instrument 110 while not in use.

Clause 13: The system 100 according to Clause 12, wherein the ultracapacitor 140 is further configured to disperse the electric potential energy to provide power to the surgical instrument 110 while in use.

Clause 14: The system 100 according to any one of Clauses 1-13, wherein the sealed enclosure 160 further comprises a thermal mass member 170 configured to absorb thermal energy generated from the ultracapacitor 140.

Clause 15: The system 100 according to Clause 14, wherein the thermal mass member 170 is a ceramic plate.

Clause 16: The system 100 according to any one of Clauses 1-15, wherein the sealed enclosure 160 is a three dimensional (3D) printed enclosure.

Clause 17: The system 100 according to any one of Clauses 1-16, wherein the sealed enclosure 160 is further configured to withstand a temperature range of approximately 121° C.-132° C.

Clause 18: The system 100 according to any one of Clauses 1-17, wherein the sealed enclosure 160 is further configured to withstand a pressure range of approximately 15-30 psi.

Clause 19: The system 100 according to Clause 18 wherein the sealed enclosure 160 is further configured to withstand a pressure of 30 psi greater than 3 minutes.

Clause 20: The system 100 according to Clause 18, wherein the sealed enclosure 160 is further configured to withstand a pressure of 15 psi for at least 15 minutes.

Any of the examples or embodiments described herein may include various other features in addition to or in lieu of those described above. The teachings, expressions, embodiments, examples, etc. described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes.

Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

What is claimed is:

1. A sterilizable powered electronics system for a surgical instrument, comprising:

a boost regulator circuit configured to electrically connect to one or more batteries and configured to output at least one of a predetermined voltage or a predetermined current;

an ultracapacitor electrically connected to the boost regulator circuit; and a sealed enclosure configured to withstand temperatures greater than 50° C. and pressures greater than 15 psi, and enclosing the boost regulator circuit and the ultracapacitor, wherein the sealed enclosure is configured to prevent ingress of moisture into the sealed enclosure during a steam sterilization process, wherein the sealed enclosure comprises at least one of an ultrasonic seal or a gasket seal, wherein at least one of the boost regulator circuit or the ultracapacitor is configured to be electrically connected to an instrument motor.

2. The system of claim 1, wherein the surgical instrument comprises the instrument motor configured to be electrically connected to the boost regulator circuit and the ultracapacitor.

3. The system of claim 1, wherein each of the one or more batteries are configured to be sterilized via a gamma sterilization process prior to insertion into the sealed enclosure.

4. The system of claim 1, wherein each of the one or more batteries is configured to output a maximum current of 5 amperes (A) to the boost regulator circuit.

5. The system of claim 4, wherein each of the one or more batteries is further configured to output an approximate voltage of 3.1V while outputting the maximum current.

6. The system claim 1, wherein each of the one or more batteries is a disposable CR123a battery.

7. The system of claim 1, wherein the ultrasonic seal is further configured to maintain an internal temperature within the sealed enclosure less than that of an external temperature exterior the sealed enclosure during the steam sterilization process.

8. The system of claim 1, wherein the gasket seal is further configured to maintain an internal temperature within the sealed enclosure that is less than that of an external temperature exterior the sealed enclosure during the steam sterilization process.

9. The system claim 1, wherein the ultracapacitor is configured to store the predetermined voltage and the predetermined current from the boost regulator circuit as electric potential energy for the surgical instrument while not in use.

10. The system of claim 9, wherein the ultracapacitor is further configured to disperse the electric potential energy to provide power to the surgical instrument while in use.

11. The system claim 1, wherein the sealed enclosure further comprises a thermal mass member configured to absorb thermal energy generated from the ultracapacitor.

12. The system of claim 11, wherein the thermal mass member-is a ceramic plate.

13. The system of claim 1, wherein the sealed enclosure is a three dimensional printed enclosure.

14. The system of claim 1, wherein the sealed enclosure is further configured to withstand a temperature range of approximately 121° C.-132° C.

15. A sterilizable powered electronics system for a surgical instrument, comprising:

a boost regulator circuit configured to electrically connect to one or more batteries and configured to output at least one of a predetermined voltage or a predetermined current, an ultracapacitor electrically connected to the boost regulator circuit, and a sealed enclosure configured to withstand temperatures greater than 50° C. and pressures greater than 15 psi, and enclosing the boost regulator circuit and the ultracapacitor, wherein the sealed enclosure is further configured to withstand a pressure range of approximately 15-30 psi, wherein at least one of the boost regulator circuit or the ultracapacitor is configured to be electrically connected to an instrument motor.

16. The system of claim 15 wherein the sealed enclosure is further configured to withstand a pressure of 30 psi greater than 3 minutes.

17. The system of claim 15, wherein the sealed enclosure is further configured to withstand a pressure of 15 psi for at least 15 minutes.

18. A sterilizable powered electronics system for a surgical instrument, comprising:

a boost regulator circuit configured to electrically connect to one or more batteries and configured to output at least one of a predetermined voltage or a predetermined current, an ultracapacitor electrically connected to the boost regulator circuit, wherein the ultracapacitor comprises one or more capacitor cells electrically connected in parallel with one or more resistors, the ultracapacitor electrically connected in series with the boost regulator circuit, and a sealed enclosure configured to withstand temperatures greater than 50° C. and pressures greater than 15 psi, and enclosing the boost regulator circuit and the ultracapacitor, wherein at least one of the boost regulator circuit or the ultracapacitor is configured to be electrically connected to an instrument motor.

* * * * *